United States Patent [19]

Sompayrac

[11] 4,226,851
[45] Oct. 7, 1980

[54] STABLE DENTAL COMPOSITION CONTAINING HYDROGEN PEROXIDE

[76] Inventor: Hewitt A. Sompayrac, South Main St., Society Hill, S.C. 29593

[21] Appl. No.: 56,633

[22] Filed: Jul. 11, 1979

[51] Int. Cl.³ .............. A61K 7/20; A61K 33/40; A61K 31/355
[52] U.S. Cl. .................... 424/53; 424/130; 424/284
[58] Field of Search .............. 424/53, 130, 284

[56] References Cited

U.S. PATENT DOCUMENTS 1,435,498  11/1922  Resnik ............................ 424/53

FOREIGN PATENT DOCUMENTS

| 137258 | 5/1950 | Australia | 424/130 |
| 2144249 | 3/1972 | Fed. Rep. of Germany | 424/284 |
| 2355010 | 7/1975 | Fed. Rep. of Germany | 424/53 |
| 7308019 | 11/1973 | Netherlands | 424/130 |

OTHER PUBLICATIONS

The Merck Index, 9th Ed., (1976)—item 9789—Merck & Co., Inc.
Chem. Abst. 76, 6726(g), (1972)—Washitake et al.
Chem. Abst. 84, 155688(p), (1976)—Knobloch et al.
Chem. Abst. 84, 155690(h), (1976)—Gritz et al.

*Primary Examiner*—Douglas W. Robinson
*Attorney, Agent, or Firm*—Dennison, Dennison, Meserole & Pollack

[57] ABSTRACT

A stable dental hygiene composition comprising a mixture of hydrogen peroxide and zinc chloride, the present mixture is stabilized by the addition of water-soluble vitamin E. The presence of water-soluble vitamin E in the mixture of hydrogen peroxide and zinc chloride acts to prevent the usual instability of hydrogen peroxide in a solution containing a metal salt while still allowing a desirable release of oxygen from the hydrogen peroxide when the mixture is used, that is, in the presence of organic matter.

9 Claims, No Drawings

STABLE DENTAL COMPOSITION CONTAINING HYDROGEN PEROXIDE

BACKGROUND OF THE INVENTION

1. Field of the Invention

The invention relates generally to hygienic compositions of matter useful particularly as dentifrices which also exhibit germicidal activity.

2. Description of the Prior Art

Dentifrice compositions have long been employed which contain therapeutic and prophylactic agents intended to destroy bacteria which find highly favorable growth conditions in accumulated food particles which lodge between the teeth and in the plaque film which forms on the surfaces of the teeth. Such compositions have often been mixed with abrasives to provide the compositions normally referred to as dentifrices. Similar compositions which do not contain abrasives and which are usually referred to as hygienic compositions or "mouth washes" are particulary used to create antiseptic conditions in the mouth by destruction of bacteria either directly and/or by facilitating the removal of food particles and/or plaque film on which bacteria thrive. The oral hygienic compositions often contain ingredients which are astringent in order that the mucous membrane can be shrunk or which are effective for desensitizing the teeth. In order to be acceptable for these uses, dentifrice and oral hygiene compositions (which will be hereinafter referred to interchangeably) must not harm sensitive oral tissues, must not react unfavorably with the teeth, and must not be harmful if swallowed. Many powerful oxidizing agents, such as those which strongly liberate chlorine, are thus unsuited for use in the dental care environment.

The prior art has provided compositions, even chlorine-liberating compositions, which have proven useful at least to some degree. In particular, Resnik, in U.S. Pat. No. 1,435,498, provides a dentifrice comprised of a hypoclorite chlorine-releasing agent. Omohundro, in U.S. Pat. No. 2,317,297, teaches the use of active oxygen-releasing agents in a dentifrice, the agents releasing either hydrogen peroxide as an intermediate or oxygen immediately upon use.

Mouth washes have also been long available which use zinc chloride as an antiseptic and astringent agent and which is intended to promote the healing of wounds and also to desensitize the teeth. As is thus apparent, hydrogen peroxide and zinc chloride have long been used separately as therapeutic agents which at least incidentally exhibit germicidal activity. Hydrogen peroxide owes germicidal activity to oxygen release which, due to the kinetics of the release, provides a mechanical as well as a chemical mechanism for cleansing wounds and also for removing tissue and other debris from inaccessible areas such as from between the teeth. The oxygen release of hydrogen peroxide is particularly pronounced in the presence of organic matter, reducing agents, metals, and metal salts. Since zinc chloride is also an effective germicidal agent, a combination of hydrogen peroxide with zinc chloride would hold promise as an effective germicidal combination which would particularly be effective as a hygienic dentifrice composition. However, combinations of hydrogen peroxide and zinc chloride have not been generally utilized due to the fact that hydrogen peroxide, as indicated above, liberates oxygen in the presence of metal salts. Accordingly, solutions of hydrogen peroxide to which zinc chloride has been added have been inherently unstable, oxygen release occurring within a time period which is sufficiently short as to render the shelf life of the mixture unacceptable. While hydrogen peroxide or zinc chloride have at times been mixed immediately prior to use, especially in the clinical environment, in order to obtain those benefits previously alluded to, this desirable combination of hygienic germicidal agents has not come into general clinical use and is effectively unavailable for general public use due to the instability of the mixture.

Various stabilizing agents have been proposed for extending the shelf life of a hydrogen peroxide/zinc chloride mixture. These agents have proven essentially worthless due to the fact that certain of the agents have been ineffective in preventing hydrogen peroxide decomposition, that is, oxygen release, while other stabilizing agents have actually stabilized the mixture to such a degree that the effectiveness of the mixture is impaired due to a reduced oxygen release. The present invention provides a stabilized hydrogen peroxide hygienic composition which also exhibits the additional antiseptic, healing, and desensitizing benefits obtained from the use of zinc chloride. In particular, the present invention provides a composition of matter containing both hydrogen peroxide and zinc chloride, which composition of matter is stabilized by the addition of water soluble vitamin E to the extent that the composition has an acceptable useful shelf life and is still sufficiently active to release oxygen on contact with organic matter such as occurs when the composition is utilized as an oral hygienic solution. The present invention therefore provides a useful oral hygienic composition of matter which avoids the problems encountered in the previous use of solutions containing both hydrogen peroxide and metal salts such as zinc chloride.

SUMMARY OF THE INVENTION

The present invention provides a chemically stable oral hygienic composition of matter comprised of hydrogen peroxide and zinc chloride, the composition of matter containing water-soluble vitamin E in an effective amount as the stabilizing agent. The present composition of matter is sufficiently stable, that is, oxygen release is effectively inhibited, to allow storage of the mixture between usages, thereby eliminating the previous need to prepare fresh solutions each time such a solution was needed. This prior inconvenience limited the use of hydrogen peroxide/zinc chloride mixtures to use in the clinical environment, a use even in the dental clinic being restricted due to this inconvenience. The present composition of matter further provides increased oxygen-liberating capability on use of the composition of matter in a dentifrice or other hygienic composition.

The present composition of matter typically is comprised of a mixture of equal parts of hydrogen peroxide (U.S. Pharmacopoeia 10 Vol. 3%) with a flavored mouth wash solution containing 2% zinc chloride. Percentages of hydrogen peroxide and zinc chloride can of course vary within established useful limits. To this mixture is added water-soluble vitamin E in a preferred ratio of approximately 7000 I.U. of vitamin E to approximately eight ounces of the bulk mixture of hydrogen peroxide and zinc chloride. It is to be understood that vitamin E can be present in the resulting stabilized mixture in greater or lesser relative quantities. In particular, since stabilization of hydrogen peroxide/zinc chloride mixtures appear to be enhanced by the presence of massive quantities of water-soluble vitamin E, it is especially within the scope of the invention to employ greater relative quantities of the stabilizing vitamin E component. Quantities somewhat less than the particularly indicated quantity of water-soluble vitamin E can, of course, be employed as long an effective amount of vitamin E is employed to render the mixture stable or desired temporal interval.

The stabilized oral hygienic composition of matter formulated according to the present invention is germicidally active due both to the presence of hydrogen peroxide and zinc chloride, the hydrogen peroxide also providing a mechanical mechanism for removing tissue and other debris from the physical use environment, such as from between the teeth when the composition of matter is employed as an oral hygienic solution or dentifrice. The mechanical mechanism, as well as the hydrogen peroxide-related chemically oxidative mechanism which operates to destroy bacteria, depends on the kinetically rapid release of oxygen by the hydrogen peroxide component of the mixture. This oxygen release is not inhibited by the presence of the stabilizing vitamin E once contact with organic matter is made, such as when the stabilized mixture is actually used. According to a particularly unexpected teaching of the invention, the release of oxygen on use of the stabilized mixture is actually increased as much as four-fold. Vitamin E therefore functions not only to stabilize hydrogen peroxide in solution when mixed with zinc chloride but also to increase the kinetic release of oxygen by the mixture. The mechanical action of oxygen release is therefore increased to more effectively remove tissue and other debris from the use environment. The benefits of improved storage capability and increased oxygen release of the hydrogen peroxide/zinc chloride mixture are also seen to be provided without sacrifice of the therapeutic and prophylactic advantages normally expected from the presence of zinc chloride in an oral hygienic composition as has been described above.

Accordingly, it is an object of the invention to provide a stabilized mixture of hydrogen peroxide and a metal salt which is stable under normal conditions of storage and which thus allow the use of such a mixture in clinical and other use situations, the mixture being stabilized by the addition of an effective amount of water-soluble vitamin E to the mixture.

It is another object of the invention to provide a composition of matter comprised of hydrogen peroxide and which is stabilized by the presence of an effective amount of water-soluble vitamin E, the kinetics of oxygen release being increased by the vitamin E on contact between the mixture and organic matter present in a use environment.

It is a further object of the invention to provide a therapeutic and prophylactic mixture of hydrogen peroxide and zinc chloride which is particularly useful as an oral hygienic composition of matter and which retains and/or improves the therapeutic capabilities of the major germicidal and antiseptic components of the mixture, which mixture is stabilized and improved by the presence of an effective amount of water-soluble vitamin E.

Other objects and advantages of the invention will become more readily apparent in light of the following detailed description of the preferred embodiments.

DESCRIPTION OF THE PREFERRED EMBODIMENTS

Mixtures of hydrogen peroxide and zinc chloride in aqueous solution are stabilized for extended temporal intervals without inhibition of oxygen release on use by the presence of an effective amount of water-soluble vitamin E in such mixtures. The stabilized mixtures are effective inter alia as oral hygienic solutions, the benefits previously known for hydrogen peroxide and zinc chloride germicidal solutions both separately and admixed together being exhibited by the present stabilized mixture. Hydrogen peroxide is known to be germicidally active due to the release of an active oxidizing agent, that is, oxygen. Further, the rapid oxygen release associated with hydrogen peroxide decomposition provides a mechanical mechanism for dislodging and displacing unwanted debris from between the teeth when hydrogen peroxide is used in a dentifrice or mouth wash. In the present composition of matter, hydrogen peroxide is stabilized in spite of the presence of a metal salt, in particular zinc chloride, in the composition of matter by the presence of an effective amount of water-soluble vitamin E, a form of alpha-tocopherol. The stabilization afforded by the presence of vitamin E in the mixture prevents unwanted oxygen release by the mixture during storage. On use of the mixture, such as in the oral cavity as a dentifrice or mouth wash, oxygen release by the hydrogen peroxide is not only not impaired by the presence of the stabilizing vitamin E, but is actually increased by the presence of vitamin E. This increase is as great as four times the regular oxygen liberation expected from a solution containing only hydrogen peroxide or from a mixture of hydrogen peroxide and zinc chloride mixed immediately prior to use (to avoid decomposition which occurs on storage even for short periods of time). The use of water-soluble vitamin E in a mixture of hydrogen peroxide and a metal salt such as zinc chloride not only provides the unexpected benefit of stabilizing the mixture (by preventing any substantial oxygen release) but also unexpectedly enhances the release of oxygen on exposure of the mixture to organic matter. Thus, the use of vitamin E as disclosed herein not only stabilizes mixtures of hydrogen peroxide and zinc chloride without reducing the effectiveness of hydrogen peroxide on use, the use of vitamin E in said mixtures also actually acts to increase oxygen release and thereby to improve the effectiveness of the mixtures. The increased storage life and improved oxygen release capability of the compositions of matter according to the present invention are provided without detriment to the effectiveness of the metal salt, for example, zinc chloride, in the mixture. The effectiveness of hydrogen peroxide in the mixture is actually seen to be improved as indicated above in a manner not associated with the increased storage life produced by the addition of water soluble vitamin E in the mixture.

In a preferred formulation, equal parts of a standard 3% solution of hydrogen peroxide (U.S.P. 10 Vol. 3%) and a solution of 2% zinc chloride (both solutions being preferably aqueous) are mixed to form a useful composition of matter such as would be employed as a mouth wash or similar oral hygienic composition of matter. The mixture could be flavored in a known manner to increase the acceptability of the mixture to a user. The mixture is stabilized by the addition of an effective amount of water-soluble vitamin E, the vitamin E providing an anti-oxidant capability which effectively prevents oxygen liberation by the mixture until contact occurs between the mixture and organic matter. The relative quantity of vitamin E required is approximately 7000 I.U. per eight ounces of the mixture, greater amounts of vitamin E being readily used without producing a detriment to the release of oxygen on use of the stabilized mixture. The antiseptic, astringent, healing, and desensitizing effects of the metal salt, for example, zinc chloride, are not compromised in the stabilized mixture by the presence of vitamin E.

While vitamin E in any form will be effective according to the invention, a water-soluble from of alpha-tocopherol is most suited to a practice of the invention due to the desirability of using an aqueous solution to facilitate solution of the metal salt component in the mixture as well as to mix well with solutions of hydrogen peroxide which are typically aqueous. While the naturally occurring form of alpha-tocopherol, that is, vitamin E, is practically insoluble in water, sufficient amounts can be brought into solution to effect the stabilization taught herein. As is well-known in the art, the international unit (I.U.) of vitamin E is equal to 1 milligram of standard dl-alpha-tocopherol acetate.

EXAMPLE

Equal volumes of aqueous solutions of nominally 3% hydrogen peroxide and nominally 2% zinc chloride were mixed to form eight ounces of a germicidally active mixture. Approximately 7000 I.U. of water solubilized vitamin E was added to the mixture of hydrogen peroxide and zinc chloride. The mixture was stoppered and stored at room temperatures for periods of time of between three days and one week without noticeable loss of oxygen-release capability. Since no decomposition has been noted after these time periods, it is expected that the stabilized mixtures are stable for greater periods of time than those which are proven by actual testing. The mixtures thus formulated and stored were used as oral hygienic solutions and were found to exhibit expected germicidal and therapeutic activity with increased rates of oxygen release up to four times the oxygen release rate expected.

It is to be understood that the present stabilized mixtures of hydrogen peroxide and zinc chloride can be formulated with varying relative amounts of vitamin E without departing from the scope of the invention. The invention, including the methods associated with the practice thereof, can thus be practiced other than as expressly described herein, the scope of the legal privilege afforded to the invention being defined by the recitations of the appended claims.

What is claimed is:

1. A composition of matter comprising a mixture of oral hygenic effective aqueous solution of hydrogen peroxide and zinc chloride, and an effective amount of vitamin E for stabilizing the mixture against oxygen release therefrom during storage.

2. The composition of matter of claim 1 wherein hydrogen peroxide and zinc chloride are present in the mixture in respective equal volumes of aqueous solutions of three percent hydrogen peroxide and two percent zinc chloride.

3. The composition of matter of claim 2 wherein vitamin E is present in a ratio of at least 7000 I.U. of vitamin E to approximately eight ounces of the mixture.

4. The composition of claim 1 wherein the composition of matter comprises a therapeutic and prophylactic oral hygienic solution.

5. The composition of matter of claim 1 wherein the vitamin E is water solubilized.

6. A method for stabilizing a mixture of oral hygenic effective aqueous solution of hydrogen peroxide and zinc chloride to increase the storage capability of the mixture comprising the step of admixing an effective amount of vitamin E with the mixture for stabalizing the mixture against oxygen release therefrom during storage.

7. The method of claim 6 wherein the vitamin E is present in the mixture in a ratio of at least 7000 I.U. of vitamin E to eight ounces of the mixture.

8. The method of claim 7 wherein the mixture is formed of respective equal volumes of aqueous solutions of three percent hydrogen peroxide and two percent zinc chloride.

9. The method of claim 6 wherein the vitamin E is water solubilized.

* * * * *